(12) United States Patent
Kim et al.

(10) Patent No.: US 12,128,245 B2
(45) Date of Patent: Oct. 29, 2024

(54) RF MICROCHIP FOR INDUCTION OF CANCER CELLS MIGRATION FOR RADIO FREQUENCY THERMAL THERAPY FOR CANCER TREATMENT OR REMOVAL SURGERY

(71) Applicant: KWANGWOON UNIVERSITY INDUSTRY-ACADEMIC COLLABORATION FOUNDATION, Seoul (KR)

(72) Inventors: Nam Young Kim, Gwangju-si (KR); Eun Seong Kim, Gwangju-si (KR)

(73) Assignee: KWANGWOON UNIVERSITY INDUSTRY-ACADEMIC COLLABORATION FOUNDATION, Seoul (KR)

(*) Notice: Subject to any disclaimer, the term of this patent is extended or adjusted under 35 U.S.C. 154(b) by 1058 days.

(21) Appl. No.: 17/045,785

(22) PCT Filed: Apr. 12, 2019

(86) PCT No.: PCT/KR2019/004430
§ 371 (c)(1),
(2) Date: Oct. 7, 2020

(87) PCT Pub. No.: WO2019/199111
PCT Pub. Date: Oct. 17, 2019

(65) Prior Publication Data
US 2021/0153925 A1  May 27, 2021

(30) Foreign Application Priority Data
Apr. 13, 2018 (KR) .......................... 10-2018-0043578

(51) Int. Cl.
*A61N 1/40* (2006.01)
*A61B 18/00* (2006.01)
(Continued)

(52) U.S. Cl.
CPC ........... *A61N 1/40* (2013.01); *A61N 1/36002* (2017.08); *A61B 2018/00333* (2013.01);
(Continued)

(58) Field of Classification Search
CPC ................................................ A61N 1/36002
See application file for complete search history.

(56) References Cited

U.S. PATENT DOCUMENTS

2006/0206173 A1    9/2006  Gertner et al.
2015/0157404 A1*   6/2015  Peyman ................. A61N 1/406
                                                 606/33

FOREIGN PATENT DOCUMENTS

JP      2007-536016 A    12/2007
KR  10-2015-0048151 A     5/2015

OTHER PUBLICATIONS

Matthew J. Ware, et al., "Radiofrequency treatment alters cancer cell phenotype", Scientific Reports, Jul. 13, 2015, pp. 1-14, vol. 5, Article No. 12083.
(Continued)

*Primary Examiner* — Michael W Kahelin
(74) *Attorney, Agent, or Firm* — Sughrue Mion, PLLC (57) ABSTRACT

A device for inducing migration of cancer cells for cancer treatment includes an RF absorber including an antenna for irradiating a living tissue including cancer cells with an RF frequency of a specific band for cancer treatment.

4 Claims, 9 Drawing Sheets

(51) Int. Cl.
*A61B 18/12* (2006.01)
*A61B 18/18* (2006.01)
*A61N 1/36* (2006.01)
*A61N 5/04* (2006.01)

(52) U.S. Cl.
CPC ............... *A61B 2018/00446* (2013.01); *A61B 2018/00452* (2013.01); *A61B 2018/00494* (2013.01); *A61B 2018/00511* (2013.01); *A61B 2018/00517* (2013.01); *A61B 2018/00529* (2013.01); *A61B 2018/00541* (2013.01); *A61B 2018/00547* (2013.01); *A61B 2018/00559* (2013.01); *A61B 18/12* (2013.01); *A61B 18/1815* (2013.01); *A61N 5/045* (2013.01)

(56) References Cited

OTHER PUBLICATIONS

International Search Report for PCT/KR2019/004430 dated Jul. 23, 2019 (PCT/ISA/210).

* cited by examiner

RF MICROCHIP FOR INDUCTION OF CANCER CELLS MIGRATION FOR RADIO FREQUENCY THERMAL THERAPY FOR CANCER TREATMENT OR REMOVAL SURGERY

CROSS REFERENCE TO RELATED APPLICATIONS

This application is a National Stage of International Application No. PCT/KR2019/004430, filed Apr. 12, 2019, claiming priority based on Korean Patent Application No. 10-2018-0043578 filed Apr. 13, 2018, the disclosures of which are herein incorporated in their entireties.

FIELD OF THE INVENTION

The present invention relates to a radio frequency (RF) microchip for inducing migration of cancer cells for microwave thermal treatment of 41 to 46° C. or removal surgery by using an RF absorber for irradiating a living tissue including cancer cells of solid cancer with a frequency of 10 to 200 mW and 13 to 14 MHz for cancer treatment.

BACKGROUND OF THE INVENTION

Cancer is a disease that occurs locally and spreads throughout the body, and it is an important disease competing for first or second place among the causes of adult death in Korea. Despite many studies on cancer treatment, about half of cancer patients eventually die. According to the statistics of cancer incidence rate (2016) announced by the Central Cancer Registration Headquarters of the Ministry of Health and Welfare in Korea, there are 214,000 new cancer patients annually in Korea, and the number of cancer patients from 1999 to 2015 is estimated to be 1.61 million. In addition, due to the westernization of dietary life and rapid aging of population, incidence of cancer patients and the death toll according thereto are expected to increase.

Cancer treatment widely used until today includes chemotherapy for anticancer treatments and surgical operation. The chemotherapy for anticancer treatments generally refers to chemotherapeutic agents excluding surgery or radiotherapy among the methods used to treat a malignant tumor, and most of them are substances exhibiting anticancer activities mainly by hindering synthesis of nucleic acids. For example, compounds such as paclitaxel, docetaxel and the like are approved by the US Food and Drug Administration and have been actually using in clinical practice, and thereby provide effect by excessively stabilizing microtubules of cells to suppress division of normal cells. However, these anticancer drugs damage normal cells, especially, normal tissues with active cell division, in addition to cancer cells, while occurring side effects such as mucosa damage of gastrointestinal tract, hair loss, stomachache, and the like, and resulting in decrease of its therapeutic efficacy by half due to the severe toxicity of the drug itself, as well as its low solubility in aqueous solution.

In addition, the surgical operation is one of the most effective radical cancer treatments since it surgically removes tissues including a tumor. However, when the tumor is removed by the surgical operation, normal tissues around the tumor, i.e., margin tissues, are resected together, and usually, 0.5 to 2 Cm of the margin tissues around the entire tumor are resected together. Therefore, it is difficult to apply the treatment when lesion sites are scattered throughout the tissues or organs.

Recently, as a new cancer treatment, interest in technologies using an RF frequency or the like is increasing. Microwave thermal treatment, which is one of the new cancer treatments, is a cancer treatment that causes necrosis of tumor tissues by electric needle for generating RF frequency into tumor tissues using ultrasound or CT and then flowing AC current of high frequency load from an electrode connected to a generator so that RF frequency is generated from the electric needle and heat is generated around the electric needle accordingly thereto. Although this is a local treatment that can effectively treat tumors non-surgically, this also has some limits to be capable of expecting the therapeutic effect only if the tumor size is 3 Cm or less and the number of tumor tissues is three or less generally.

Under the technical background like this, it is required to develop multidirectional treatment technologies that can obtain a significant cancer treatment effect on lesions distributed in a widely area, as well as local lesions in the early stage of cancer onset.

SUMMARY OF THE INVENTION

Therefore, to solve the above problems, and an object of the present invention is to provide a device for inducing migration of cancer cells for cancer treatment, in which the device comprises an RF absorber for inducing migration of cancer cells including an antenna for irradiating a living tissue including cancer cells with a frequency in a range of 13 to 14 MHz, and the frequency irradiated from the antenna induces migration of the cancel cells, wherein the RF absorber includes a power supplier; an LC oscillator configured to have an inductor (L) and a capacitor (C); a modulator using a modulation method of AM, FM, ASK, and FSK to irradiate an RF frequency modulated signal; a bandpass filter having a center frequency in a range of 13 to 14 MHz and a bandwidth of 1 to 2 MHz; an amplifier for amplifying a signal having a frequency in a range of 13 to 14 MHz; and an antenna, wherein the RF absorber is implanted in or attached to a surface of one end of the living tissue, so as to move the cancer cells to an area at one side of the living tissue, where the RF absorber is implanted or attached.

To accomplish the above objects, according to one aspect of the present invention, there is provided a device for inducing migration of cancer cells for cancer treatment, comprising an RF absorber including an antenna for irradiating a living tissue including cancer cells with a frequency in a range of 13 to 14 MHZ, and the frequency irradiated from the antenna induces migration of the cancel cells.

The term "cancer" used in this specification generally means a disease caused by cells having an aggressive property of dividing and growing while ignoring normal growth limits, an invasive property of invading surrounding tissues, and a metastatic property of spreading to other parts of a body. The cancer may be a solid cancer, and the type of cancer according to the onset site may be selected one of a group including skin cancer, liver cancer, colorectal cancer, cervical cancer, kidney cancer, stomach cancer, prostate cancer, breast cancer, brain tumor, lung cancer, uterine cancer, colon cancer, bladder cancer, and pancreatic cancer.

The term "treatment" used in this specification generally means any behavior which improves or beneficially changes symptoms of cancer through a series of treatments including the device, and for example, it may mean moving cancer cells widely distributed in a living tissue to be collected in a local area, and removing or killing the cancer cells collected in the local area.

The term "migration of cancer cells" used in this specification may mean moving cancer cells to an area of a living tissue where the RF absorber is located. Accordingly, when cancer cells are widely distributed throughout a living tissue, it may have an effect of reducing lesion sites by moving the cancer cells to a local area. At this point, the living tissue includes a living tissue including cancer cells, and it may be understood as being limited to specific organs such as skin, liver, large intestine, cervix, kidney, stomach, prostate, breast, brain, lung, uterus, colon, bladder, and pancreas.

The RF absorber constituting the device for moving cancer cells according to an embodiment is a configuration for irradiating a living tissue with a frequency in a range of 13 to 14 MHz, and may be manufactured in a form having various materials and shapes known in the art. For example, it may be provided in the form of a chip of a micro unit. In addition, an antenna capable of irradiating a frequency of a specific band may be included at one side of the RF absorber while the RF absorber opposes or contacts the living tissue. The antenna is located at a surface closest to the living tissue in the RF absorber and may include a structure known in the art for transmitting/receiving the frequency, for example, a cavity backed log spiral conductive structure. The RF absorber may be used while opposing or being implanted in or attached to the living tissue, and at this point, the frequency of a specific band irradiated from the antenna of the RF absorber, for example, a frequency of 13.56 MHz of the RF absorber, may move cancer cells to a local area in the living tissue.

In an embodiment, the RF absorber may be provided in the form of a microchip, and the integrated circuit of the RF absorber may include a power supplier; an LC oscillator configured of an inductor (L) and a capacitor (C); a modulator using a modulation method of AM, FM, ASK, and FSK to irradiate an RF frequency modulated signal; a bandpass filter having a center frequency in a range of 13 to 14 MHz and a bandwidth of 1 to 2 MHz; an amplifier for amplifying a signal having a frequency in a range of 13 to 14 MHz, and an antenna, which are mounted on the microchip. In addition, a control unit and a Bluetooth communication unit of the RF absorber known in the art and involved in the ON/OFF operation of the RF absorber may be separately provided.

According to another aspect of the present invention, there is provided a method for inducing migration of cancer cells, comprising the step of generating a frequency in a range of 13 to 14 MHz by operating an RF absorber implanted in or attached to a living tissue including cancer cells.

The terms "cancer", "treatment", "migration of cancer cells", and "RF absorber" are as described above.

In an embodiment, the method may have an effect of reducing lesion sites by moving cancer cells widely distributed throughout a living tissue to a local area, for example, an area at one side of the living tissue, where the RF absorber is implanted or attached, by irradiating the living tissue including cancer cells with a frequency of a specific band. Therefore, the effect of treating a cancer can be improved by performing the method described above before performing a surgical operation or a cancer treatment such as microwave thermal treatment using RF frequency in a local area.

According to still another aspect of the present invention, there is provided a method for cancer treatment, comprising the steps of: (a) generating a frequency in a range of 13 to 14 MHz by operating an RF absorber implanted in or attached to a living tissue including cancer cells; and (b) removing cancer cells moved by the frequency.

The terms "cancer", "treatment", "migration of cancer cells", and "RF absorber" are as described above.

The living tissue is originated from an entity including cancer cells, that is, it may mean a living tissue of a cancer patient. The entity may be a vertebrate, specifically a mammal, an amphibian, a reptile, a bird, or the like, and more specifically a mammal, for example, a human being (*Homo sapiens*).

The step of removing cancer cells may mean all sorts of behaviors for killing the cancer cells or reducing their functionality, as well as separating the cancer cells from normal tissues in a living tissue. In addition, at the step of removing cancer cells, treatments commonly used in the field of cancer treatment may be used individually or in combination. For example, a local treatment of cancer may be applied individually, or both the local treatment and systemic treatment may be applied simultaneously, separately, or sequentially. In an embodiment, the step of removing cancer cells may be selected one of a surgical operation (resection), a microwave thermal treatment using RF frequency, irradiation of an RF frequency, and a combination of these.

Advantageous Effects

The device and method according to the present invention may apply a frequency in a range of 13 to 14 MHz to a living tissue including cancer cells to move the cancer cells to an area on a surface of one end of the living tissue by operating an RF absorber, and may remove the moved cancer cells through resection, microwave thermal treatment by using RF frequency, or irradiation of RF frequency.

This technology is expected to be applied as a core technology in the field of cancer treatment as it is less harmful to human body than conventional chemotherapy or radiotherapy and may remove cancer cells more effectively.

DETAILED DESCRIPTION OF THE INVENTION

Hereafter, example embodiments of the present invention will be described in detail with reference to the accompanying drawings.

The following embodiments are provided to more completely describe the present invention to those skilled in the art, and the following embodiments may be modified in various other forms, and the scope of the present invention is not limited to the following embodiments.

The terms used in this specification are used to describe specific embodiments and are not intended to limit the present invention. As used in this specification, singular forms may include plural forms unless the context clearly indicates other cases. In addition, when used herein, "comprise, include" and/or "comprising, including" specifies existence of mentioned shapes, numbers, steps, actions, members, elements, and/or groups thereof, and does not preclude the presence or addition of one or more other shapes, numbers, actions, members, elements and/or groups.

The present invention provides an RF microchip for inducing migration of cancer cells for microwave thermal treatment using RF frequency of 41 to 46° C. or removal surgery by using an RF absorber for irradiating a living tissue including cancer cells of solid cancer with a frequency of 10 to 200 mW and 13 to 14 MHz (e.g., 13.56 MHz).

Figure 1:
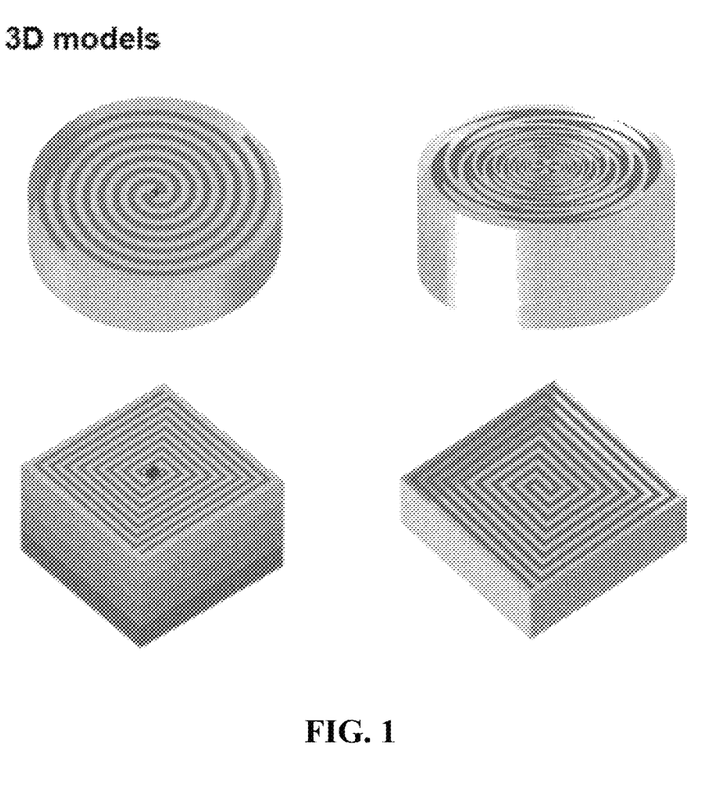
FIG. 1 is a view showing exemplary structures and shapes of an RF absorber according to a specific embodiment.
Figure 2:
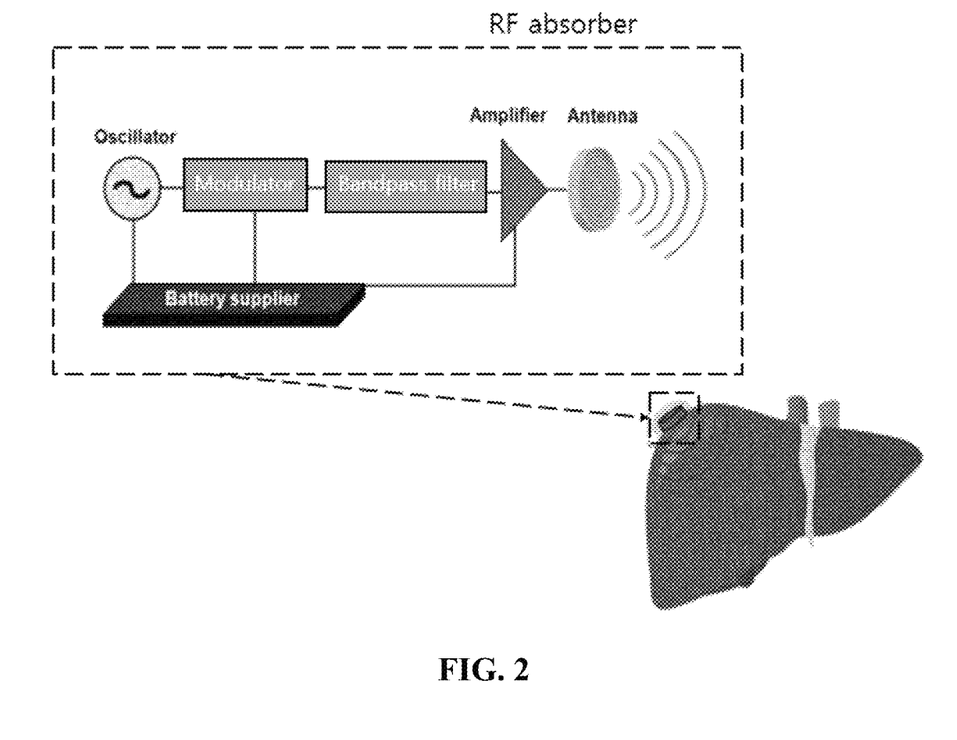
FIG. 2 is a schematic view showing the circuit of an RF absorber according to a specific embodiment.

FIGS. 1 and 2 are views showing exemplary structures and shapes of an RF absorber and a schematic view of an RF circuit according to a specific embodiment.

The RF absorber according to an embodiment is a device for generating a frequency in a range of 13 to 14 MHZ, more specifically, 13.56 MHz, and irradiating a living tissue with the frequency, and may be manufactured in various materials and shapes known in the art. For example, it may be provided in the form of a chip of a micro unit having a shape of circular cylinder or square cylinder. In addition, the RF absorber may include an antenna for transmitting a frequency to a living tissue, and the antenna may include a cavity backed log spiral conductive structure to form a frequency of a specific band. In addition, the RF absorber may be provided in the form of a microchip, and the integrated circuit of the RF absorber includes a power supplier; an LC oscillator configured of an inductor (L) and a capacitor (C); a modulator using a modulation method of AM, FM, ASK, and FSK; a bandpass filter having a center frequency of 13 to 14 MHz and a bandwidth of 1 to 2 MHz; an amplifier for amplifying a signal having a frequency of 13 to 14 MHz; and an antenna, which are mounted on the microchip, and is manufactured as a hybrid MIC, an MMIC or an SoC.

In addition, the RF absorber is provided with a micro LED driving circuit or an optical fiber driving circuit, and may further include a micro LED or an optical fiber for irradiating with near infrared (NIR) rays having a wavelength of 470 nm to 700 nm reaching the inside of a living tissue.

In addition, the RF absorber may further include a mixer, a power divider, a Balun filer or the like as needed, and a control unit and a Bluetooth communication unit of the RF absorber, which are known in the art and involved in the ON/OFF operation of the RF absorber, may be separately provided.

Figure 3:
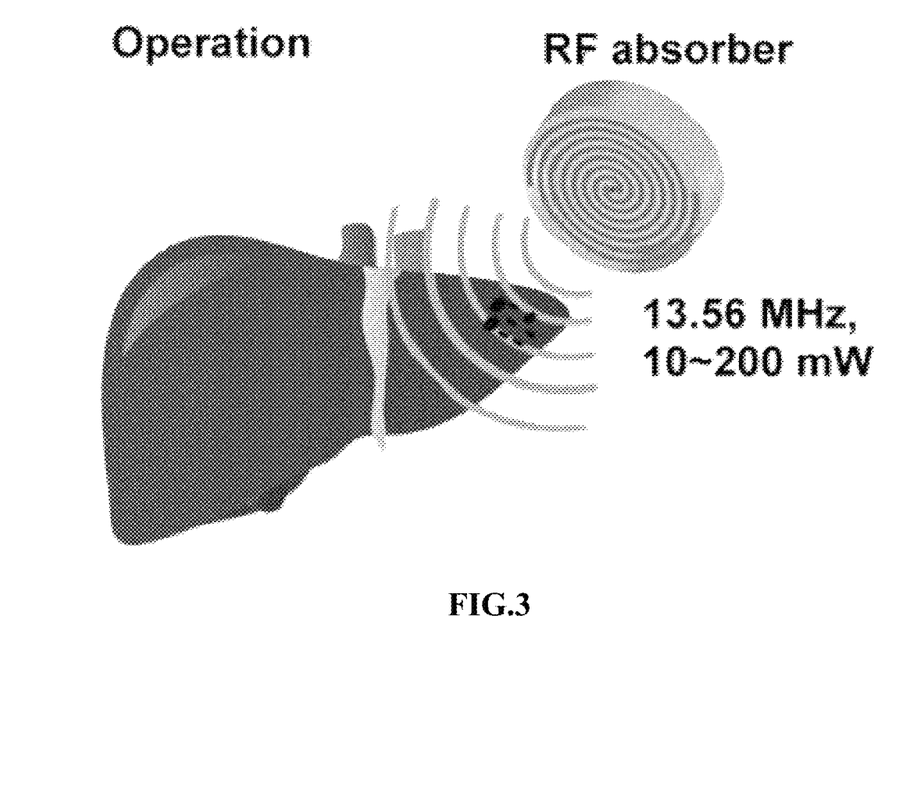
FIG. 3 is a view showing the operation process of an RF absorber according to a specific embodiment.

FIG. 3 a view showing the operation process of an RF absorber according to a specific embodiment.

The RF absorber according to an embodiment may be used while facing or being implanted in or attached to the living tissue, and at this point, the frequency of a specific band irradiated from the antenna of the RF absorber, for example, a frequency of 13.56 MHz, may have an effect of reducing a lesion site by moving cancer cells widely distributed throughout a living tissue to a local area, for example, an area at one side of the living tissue, where the RF absorber is implanted or attached.

Figure 4:
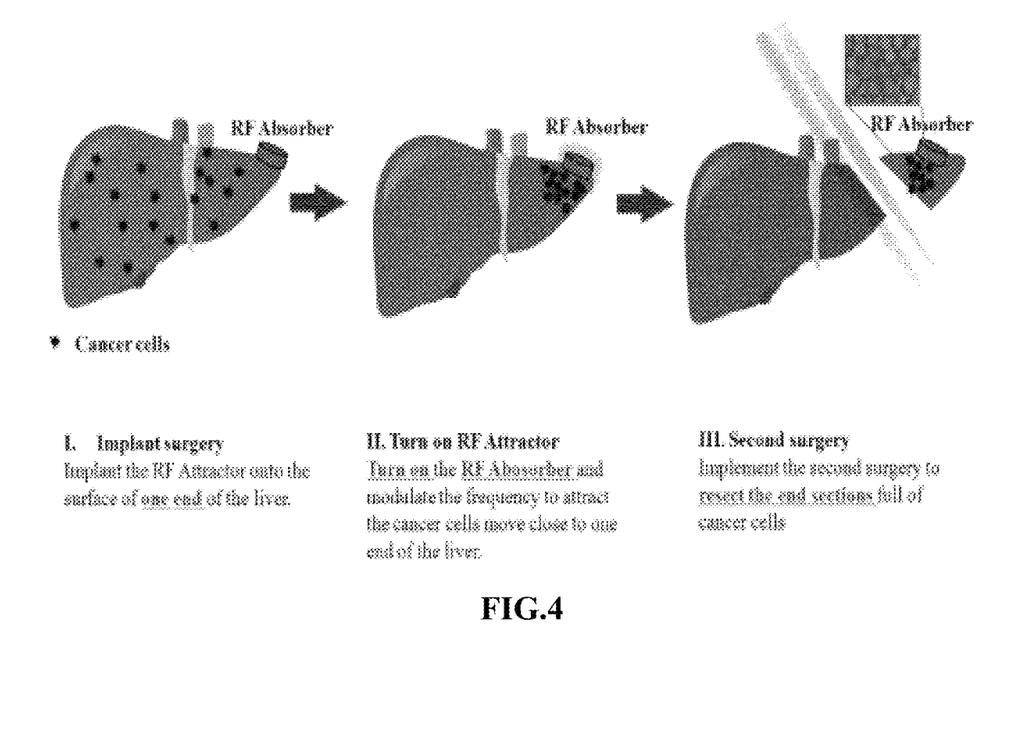
FIG. 4 is a view illustrating a method for treating cancer according to a specific embodiment, which schematically shows a series of processes of inducing migration of cancer cells by using a device according to the specific embodiment, and then resecting a tissue related thereto.
Figure 5:
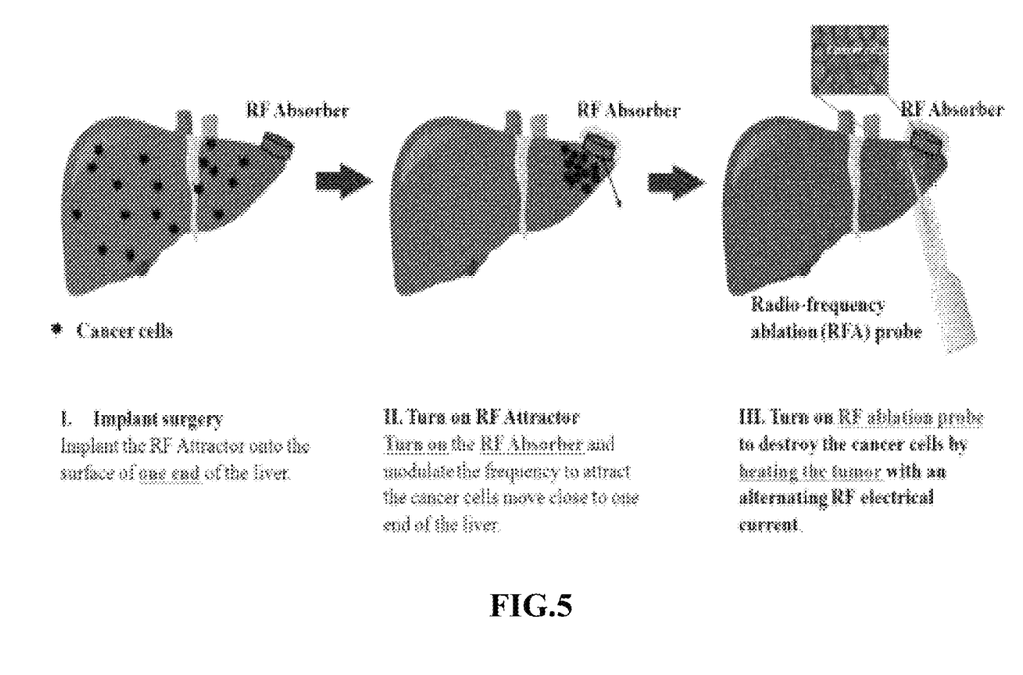
FIG. 5 is a view illustrating a method for cancer treatment according to a specific embodiment, which schematically shows a series of processes of inducing migration of cancer cells by using a device according to the specific embodiment, and then performing RF thermal treatment on a tissue related thereto.
Figure 6:
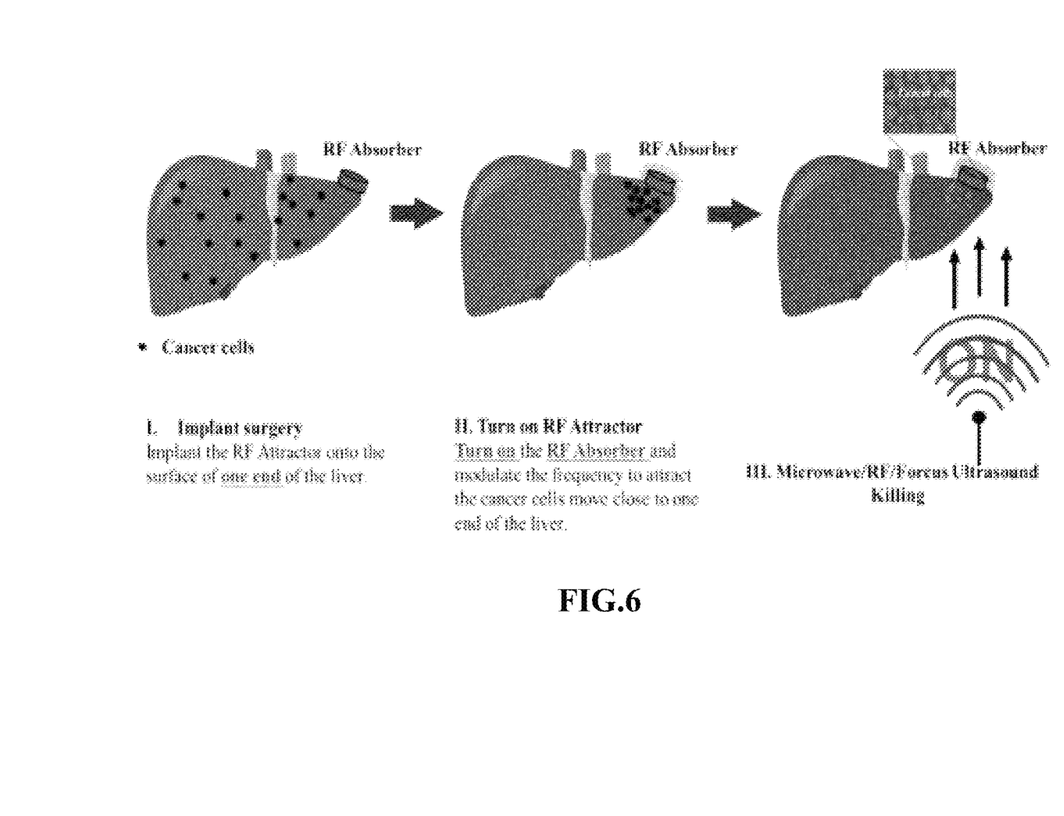
FIG. 6 is a view illustrating a method for cancer treatment according to a specific embodiment, which schematically shows a series of processes of inducing migration of cancer cells by using a device according to the specific embodiment, and then irradiating a related tissue with an RF frequency.

FIGS. 4 to 6 are views respectively illustrating a method of treating cancer according to a specific embodiment, which schematically shows a series of processes of inducing migration of cancer cells using a device according to the specific embodiment, and then resecting a tissue related thereto (FIG. 4), performing RF thermal treatment of 41 to 46° C. (FIG. 5), and irradiating an RF frequency and focused ultrasound (FIG. 6).

The method for cancer treatment according to an embodiment may include the steps of: (a) transferring a frequency in a range of 13 to 14 MHz (e.g., 13.56 MHz) to a living tissue including cancer cells by operating an RF absorber implanted in or attached to the living tissue; and (b) removing the cancer cells. At step (a), lesion sites may be reduced by moving the cancer cells widely distributed throughout the living tissue to a local area, for example, an area at one side of the living tissue, where the RF absorber is implanted or attached. Step (b) may mean all sorts of behaviors for killing the cancer cells or reducing their functionality, as well as separating the cancer cells from normal tissues in the living tissue. For example, to separate the cancer cells from normal tissues in the living tissue, a surgical operation, i.e., a surgical resection, may be applied (see FIG. 4). To kill the cancer cells or to reduce their functionality, microwave thermal treatment of 41 to 46° C. or irradiation of RF frequency may be applied.

Figure 7:
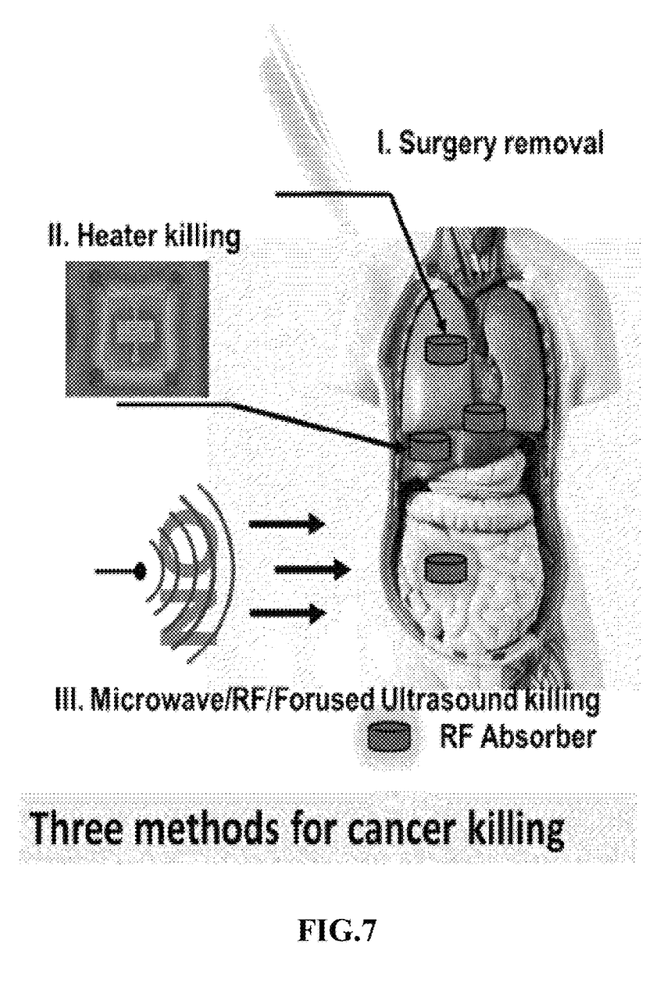
FIG. 7 is a view comprehensively showing a method of treating cancer according to a specific embodiment, which schematically shows a series of processes of inducing migration of cancer cells in various living tissues using a device according to the specific embodiment, and then performing I. Resection (surgery removal), II. Microwave thermal treatment using RF frequency (heater killing), and III. Irradiation of RF frequency and focused ultrasound (Microwave/RF/Focus Ultrasound killing) on a tissue related thereto.

FIG. 7 a view comprehensively illustrating a method of treating cancer according to a specific embodiment, which schematically shows a series of processes of inducing migration of cancer cells in various living tissues using a device according to the specific embodiment, and then performing I. Resection, II. Microwave thermal treatment using RF frequency, and III. Irradiation of RF frequency and focused ultrasound on a tissue related thereto.

The cancer treatment method according to an embodiment may be applied to a living tissue including cancer cells, and may be applied to cancer cells existing in tissues of, for example, skin, liver, large intestine, cervix, kidney, stomach, prostate, breast, brain, lung, uterus, colon, bladder, and pancreatic. In addition, when it is needed, a local treatment of cancer may be applied individually, or both the local treatment and systemic treatment may be applied simultaneously, separately, or sequentially.

Hereinafter, the present invention will be described in more detail through embodiments. However, these embodiments are for illustrative purposes, and the scope of the present invention is not limited to these embodiments.

EMBODIMENTS

Embodiment 1. Migration of Cancer Cells by RF Frequency

In this embodiment, it is attempted to confirm the effect of RF frequency on the migration of cancer cells. Specifically, using an RF absorber according to an embodiment, an RF frequency of 13.56 MHz is irradiated for 20 hours on a tissue in which cancer cells exist. Thereafter, cancer cells moved to an area in which the tissue is irradiated with the RF frequency are counted, and changes in the expression of factors related to motility or mobility in the cancer cells are evaluated. WM cells or G361 cells known as skin cancer cells are used as the cancer cells, and a group where the tissue is not irradiated with the RF frequency is set as a control group.

Figure 8:
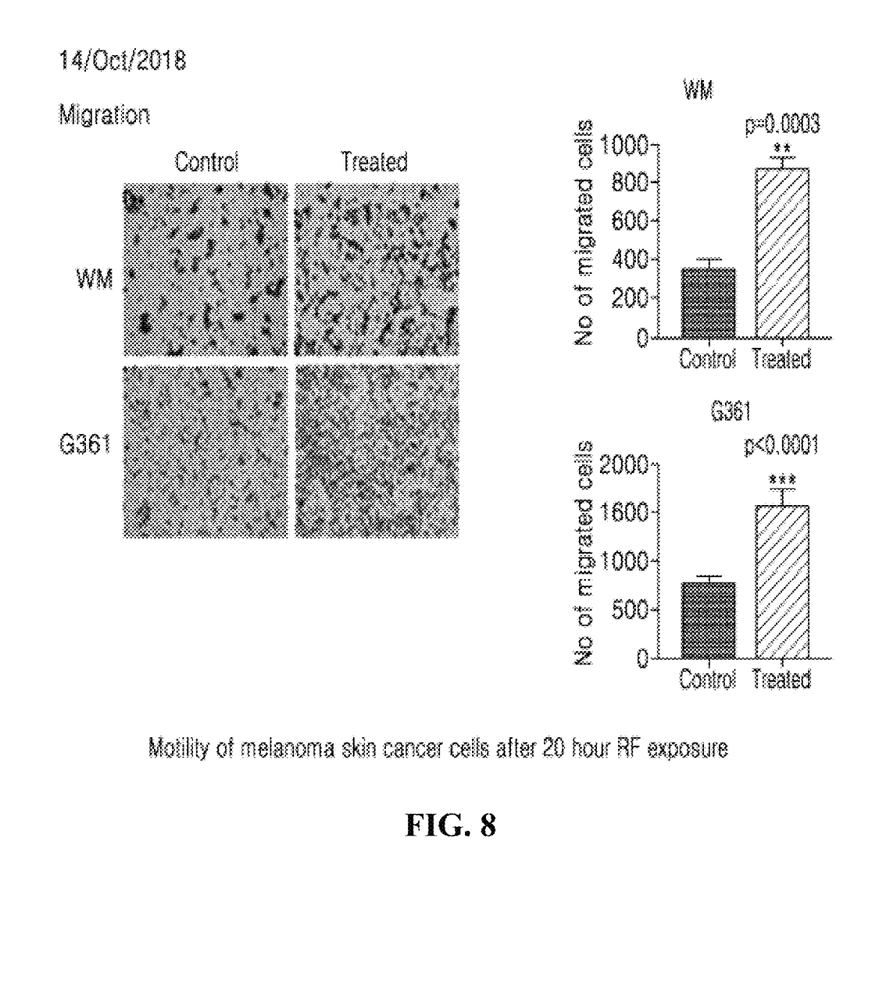
FIG. 8 is a view showing a result of counting cancer cells moved to an area in which a tissue having cancer cells is irradiated with an RF frequency of about 13.56 MHz after irradiating a tissue having cancer cells with the RF frequency for 20 hours (Control: Group not irradiated with RF frequency, Treated: Group irradiated with RF frequency).
Figure 9:
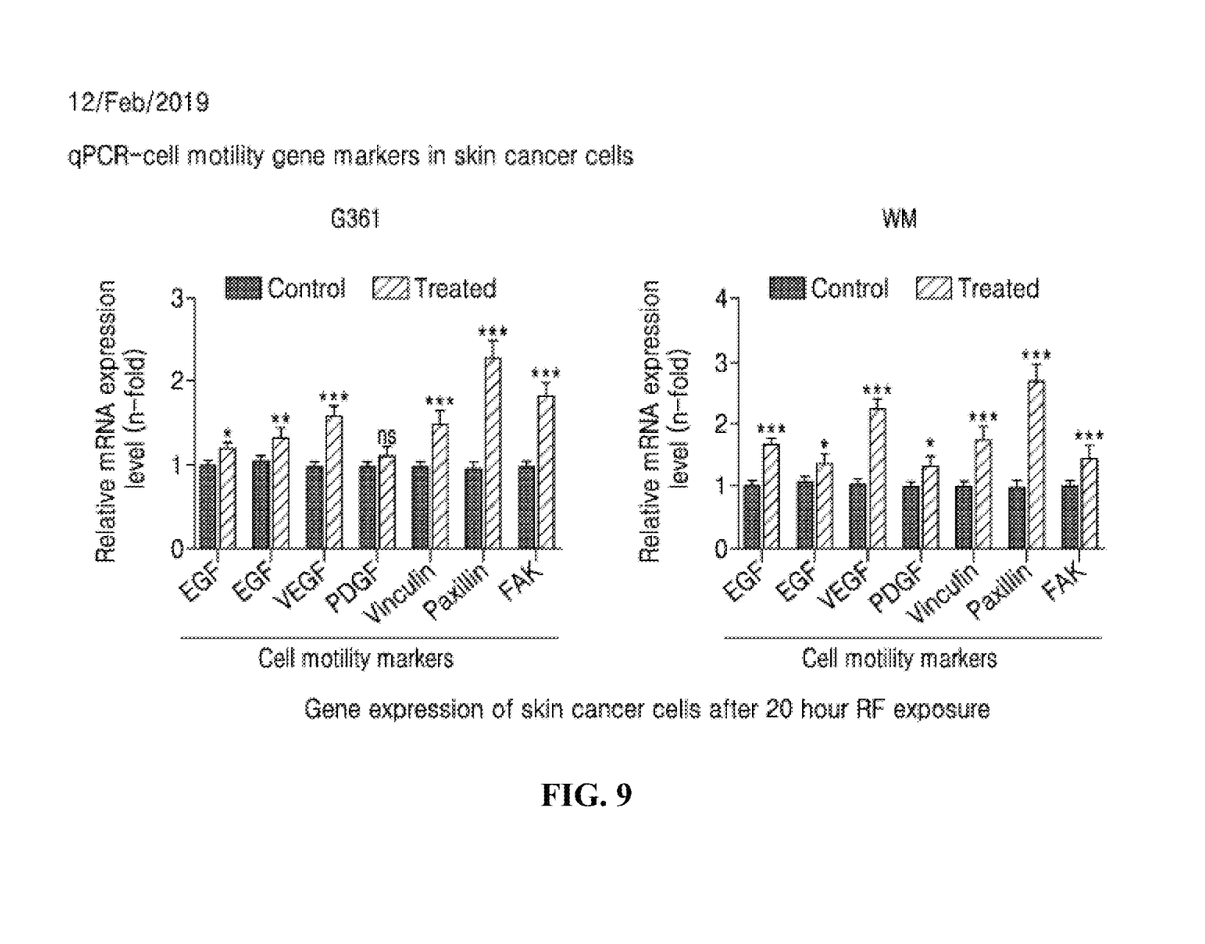
FIG. 9 is a view showing a result of confirming changes in the expression of factors related to motility in cancer cells after irradiating a tissue having cancer cells with an RF frequency of 13.56 MHz for 20 hours (Control: Group not irradiated with RF frequency, Treated: Group irradiated with RF frequency).

As a result, as shown in FIG. 8, it can be confirmed in both the WM cells and the G361 cells that a large number of cancer cells move to the area irradiated with the RF frequency, and this effect is remarkable compared to that of the control group. In addition, as shown in FIG. 9, the RF frequency improves the factors related to mobility of the cancer cells, such as EGF, FGF, and the like.

From the experiment result like this, it is known that cancer cells can be moved to an area on a surface of one end of a living tissue by applying a frequency in a range of 13 to 14 MHz to the living tissue, and therefore, cancer cells or tissues can be removed effectively.

The above description of the present invention is for illustrative purposes only, and those skilled in the art may understand that the present invention can be easily modified into another specific form without changing the technical spirit or essential features of the present invention. Therefore, it should be understood that the embodiments described above are illustrative and not restrictive in all respects.

What is claimed is:

1. A device for inducing migration of cancer cells for cancer treatment, the device comprising an RF absorber for inducing migration of cancer cells including an antenna for irradiating a living tissue including cancer cells with a frequency in a range of 13 to 14 MHz, wherein the frequency irradiated from the antenna induces migration of the cancer cells,
    wherein the RF absorber includes a power supplier; an LC oscillator configured to have an inductor (L) and a capacitor (C); a modulator using a modulation method of AM, FM, ASK, and FSK to irradiate an RF frequency modulated signal; a bandpass filter having a center frequency in a range of 13 to 14 MHz and a bandwidth of 1 to 2 MHz; an amplifier for amplifying a signal having a frequency in a range of 13 to 14 MHz; and an antenna,
    wherein the RF absorber is implantable in or attachable to a surface of one end of the living tissue, such that the cancer cells are moved to an area at the one end of the living tissue, where the RF absorber is implantable or attachable.

2. The device according to claim 1, wherein the RF absorber irradiates the living tissue with a frequency of 13.56 MHz.

3. The device according to claim 1, wherein the cancer is a solid cancer.

4. The device according to claim 1, wherein the cancer is selected one of a group including skin cancer, liver cancer, colorectal cancer, cervical cancer, kidney cancer, stomach cancer, prostate cancer, breast cancer, brain tumor, lung cancer, uterine cancer, colon cancer, bladder cancer, and pancreatic cancer.

* * * * *